United States Patent [19]

Tubaro et al.

[11] Patent Number: 4,596,711

[45] Date of Patent: Jun. 24, 1986

[54] THERAPEUTIC COMPOSITIONS OF TRICHOMONACIDE ACTIVITY, BASED ON THE TOTAL EXTRACT OF CHAMOMILE FLOWERS

[75] Inventors: Aurelia Tubaro, Goriciza; Roberto Della Loggia, Trieste; Elena Banfi, Trieste; Marina Cinco, Trieste; Claudio Redaelli, Perego, all of Italy

[73] Assignee: Bonomelli SpA, Dolzago, Italy

[21] Appl. No.: 553,057

[22] Filed: Nov. 18, 1983

[51] Int. Cl.$^4$ ............................................. A61K 35/78
[52] U.S. Cl. .................................................. 424/195.1
[58] Field of Search .......................................... 424/195

[56] References Cited

U.S. PATENT DOCUMENTS

| | | | |
|---|---|---|---|
| 1,926,929 | 9/1933 | Abelmann | 424/195 |
| 3,984,538 | 10/1974 | Korkis | 424/74 |
| 4,148,873 | 4/1979 | Owades | 424/59 |
| 4,230,689 | 10/1980 | Choy | 424/74 |

FOREIGN PATENT DOCUMENTS

| | | | |
|---|---|---|---|
| 384134 | 10/1923 | Fed. Rep. of Germany | 424/195 |
| 609884 | 2/1935 | Fed. Rep. of Germany | 424/195 |
| 1015120 | 8/1952 | France | 424/195 |

OTHER PUBLICATIONS

Chemical Abstracts, vol. 92, No. 29, Jun. 9, 1980, p. 120, No. 191892z.

Chemical Abstracts, vol. 79, No. 10, Sep. 10, 1973, p. 292, No. 57634v.

*Primary Examiner*—Stanley J. Friedman
*Assistant Examiner*—John W. Rollins
*Attorney, Agent, or Firm*—Stevens, Davis, Miller & Mosher

[57] ABSTRACT

Therapeutic compositions having strong trichomonacide activity against *Trichomonas vaginalis* have been prepared, based on the total hydro-alcoholic extract of Chamomile flowers.

2 Claims, No Drawings

THERAPEUTIC COMPOSITIONS OF TRICHOMONACIDE ACTIVITY, BASED ON THE TOTAL EXTRACT OF CHAMOMILE FLOWERS

This invention relates to therapeutic compositions based on the total extract of chamomile flowers.

More precisely, the invention relates to therapeutic compositions active against *Trichomonas vaginalis* infections and constituted essentially by the dry residue of the total hydro-alcoholic extract of chamomile flowers.

The classical system of classification derived by Limneo placed the protozoa in the animal kingdom, whereas fungi and bacteria were considered vegetable.

Although a more modern system groups these microorganisms into the protista kingdom, the biological differences between protozoa, bacteria and single-cell fungi (yeasts) are such that they constitute different phyla, just as the vertebrate phylum (fish, amphibia, reptiles, birds and mammals) is distinguished from the arthropoda phylum (crustacea, arachnids, insects etc). These differences relate to the presence or absence of sub-cellular structures, to the genetic organisation, to the biosynthetic paths etc. (R. Y. Stainer et al. in "Il dei microorganismi" Zanichelli—1975).

It is also well known that such different organisms have a totally different sensitivity to drugs, so that the pharmalogical approach provides for a sharp distinction between antimicrobial agents (antibacterials, antifungals and antibiotics) and antiparasitic agents such as antihelminthics, antimalarials, antiamebics and trichomonacides (Goodman and Gilman "The pharmacological basis of therapeutics" McMillan 1980, pages 1013-1251).

There is generally no superposing, in the sense that antibacterials and antifungals are not active against protozoa. In any case, the rare exceptions do not concern *Trichomonas vaginalis*.

Thus, the antibacterials include the sulphamides, the penicillins, the aminoglycosides, the tetracyclines, chloramphenicol, the antituberculars, the macrolides etc., and the antifungals include nystatin, amphotericin B, griseofulvin etc. None of these products is active against protozoa.

The antiparasitics (those with exclusively antiparasitic activity) include essentially the amino-quinolines and the diaminopyrimidines as antimalarials, whereas the most important amebecide and trichomonacide is metronidazole (see the previously cited work of Goodman and Gilman). This latter drug is in practice the only one used in trichomoniases, but has problems relating to its possible carcinogenicity (Harrison "Principles of internal medicine" McGraw Hill Inc. VIII Ed. 1977, page 1086).

It can therefore be stated that the problem of treating trichomoniases, which are widespread infections caused by the protozoon *Trichomonas vaginalis*, is currently unsolved.

We have now discovered the subject matter of the present invention, namely that the total hydro-alcoholic extract of chamomile flowers produced by a process which ensures total extraction of all the non-cellulose components contained therein, has considerable antiprotozoan activity, in particular against *Trichomonas vaginalis*, such as to allow the preparation of therapeutic compositions having a marked curative effect on trichomoniases.

Our discovery is completely surprising given the known resistance of *Trichimonias vaginalis* to any chemo-therapeutic agent, and given that the only therapeutic activity encountered up to the present time in chamomile extracts (infusions) is a mild bacteriostatic and fungicide activity.

Such activity, which is so irrelevant and contradictory as to have never resulted in the preparation of medicinal specialities based on chamomile infusions and having specific antibacterial activity, suggested a priori that chamomile extracts should have no activity against protozoa, and in particular against the most stubborn of these, namely *Trichomonas vaginalis*.

In order to uniquely identify the product to be claimed in the present invention and to allow its reproduction in such a manner as to ensure its consistency of composition, which is certainly very complicated in terms of the range of constituents, a detailed preparation example is given hereinafter.

EXAMPLE 10 kg of a mixture of chamomile flowers of *Matricaria chamomilla* type, normally used for preparing chamomile infusions, are infused with 55 liters of 96° ethyl alcohol and 45 liters of purified water.

The mixture is allowed to stand for one week at ambient temperature, after which the mass is pressed and the extract collected.

10 kg of the same mixture of chamomile flowers are added to the extract obtained in this manner, and the mixture again left to stand for one week at ambient temperature.

It is again pressed, and the extract of about 80 liters filtered.

This extract is evaporated to dryness, preferably under vacuum, to obtain a residue of 4 kg of dry substance.

The dry residue obtained in this manner is of very complex composition. Some identified components include chamazulene, bisabolols, bisabolol oxides, azulene dicycloethers, apigenin and apigenin glucosides. However many other unidentified components are also present.

The antiprotozoan activity of the dry residue of the hydro-alcoholic chamomile extract was tested by the series dilution method described by Meingassner et al. (Meingassner et al.—Arzneim. Forsch. 31, 6 (1981)), which leads to a Minimum Lethal Concentration (MLC) defined as the maximum dilution at which mobile (ie living) organisms are not visible under microscopic examination after a determined incubation period, and a Minimum Inhibiting Concentration (MIC) defined as the maximum dilution at which there is no growth of the inoculated population.

For the activity test, a strain of *Trichomonas vaginalis* isolated in hospital was used together with a suitable culture medium prepared as described by Diamond L. S.—J. Parasit. 48, 488 (1957).

The following table gives the data obtained for two different incubation times, namely 24 and 48 hours. The values shown represent the number of living protozoa per $mm^3$ of culture medium (mean of 4 readings±Standard Deviation) at the stated dilutions, on termination of the incubation time.

The dilutions are expressed as percentage of dry substance as heretofore prepared (ECB) diluted in the medium. The concentration expressed as mg of dry product per ml of medium is given in parentheses.

The table shows that after 48 hours, which is a time commonly used for such evaluations, the MLC is represented by the 5% concentration (2.5 mg/ml), whereas the MIC is represented by 2.5% (1.3 mg/ml).

TABLE

Activity of chamomile extract (ECB) on Trichomonas vaginalis*

| Duration | Inoculum | 0% | ECB concentrations ||||| 
|---|---|---|---|---|---|---|---|
| | | | 1.25% (0.6) | 2.5% (1.3) | 5% (2.5) | 10% (5) | 20% (10) |
| 24 h | 275 ± 15 | 710 ± 20 | 510 ± 30 | 255 ± 15 | 120 ± 10 | 0 | 0 |
| 48 h | 103 ± 16 | 835 ± 25 | 205 ± 16 | 110 ± 6 | 0 | 0 | 0 |

*The stated values represent the number of mobile protozoa per $mm^3$ ± S.D.

As stated, the total extract of chamomile flowers can be used in the form of the dry product possibly mixed with normal suitably selected diluents, solvents and excipients commonly used in medicine.

It is also possible to only partly evaporate the hydro-alcoholic solvent, and to directly use the partial concentrate.

There is obviously no toxocity or side-effect with the new trichomonacide product according to the present invention.

We claim:

1. A process for treating a patient suffering from a *Trichomonas vaginalis* infection by contacting said patient with a trichomonacidally effective amount of a therapeutic composition comprising as active principle the dry residue of the total hydro-alcoholic extract of the chamomile flowers obtained at ambient temperature and a pharmaceutically acceptable carrier, said active principle being present at concentration between 1.3 and 5 mg/ml.

2. A process as claimed in claim 1, wherein said active principle is present at a concentration between 1.3 and 2.5 mg/ml.

* * * * *